United States Patent [19]

Margolis

[11] 4,125,327

[45] Nov. 14, 1978

[54] METHOD AND APPARATUS FOR SIMULTANEOUSLY RECORDING REACTION TIMES

[75] Inventor: Joel Margolis, Sydney, Australia

[73] Assignee: Gradient Pty. Limited, Sydney, Australia

[21] Appl. No.: 737,523

[22] Filed: Nov. 1, 1976

[30] Foreign Application Priority Data

Nov. 17, 1975 [AU] Australia .............................. PC3998
Jan. 21, 1976 [AU] Australia .............................. PC4587

[51] Int. Cl.² ...................... G01N 33/16; G01N 33/00; G01N 21/24
[52] U.S. Cl. ........................................ 356/39; 356/427; 23/230 B; 422/55; 422/68
[58] Field of Search .................. 356/201, 39, 180, 208, 356/184, 197; 259/51, 52, 112, 70, 71; 23/230 B, 253 R

[56] References Cited

U.S. PATENT DOCUMENTS

| | | | |
|---|---|---|---|
| 3,635,678 | 1/1972 | Seitz | 23/253 X |
| 3,802,782 | 4/1974 | Natelson | 356/184 X |
| 3,833,864 | 9/1974 | Kiess et al. | 356/184 |
| 3,847,482 | 11/1974 | Sokol | 356/208 X |
| 4,027,979 | 6/1977 | Komarniski | 356/180 |

Primary Examiner—Vincent P. McGraw
Assistant Examiner—Rodney Bovernick
Attorney, Agent, or Firm—Haseltine, Lake & Waters

[57] ABSTRACT

An apparatus and method of determining the end point of a chemical reaction producing an optical change in a plurality of samples is disclosed. The invention is particularly suitable for the simultaneous determination of the coagulation time for multiple samples of blood and like materials.

12 Claims, 3 Drawing Figures

METHOD AND APPARATUS FOR SIMULTANEOUSLY RECORDING REACTION TIMES

FIELD OF THE INVENTION

The present invention relates to an apparatus and method for simultaneously determining the completion time for chemical reactions, which produce an optical change, in a plurality of chemical samples. The invention is particularly applicable to the rapid and accurate processing of large numbers of samples of blood and like materials to determine such qualities as clotting times, although the invention is not restricted thereto.

PRIOR ART

Hitherto coagulation tests carried out in relation to blood and associated materials have essentially only been able to be performed on single samples or, at most, two samples simultaneously. Therefore prior art methods and apparatus have not been suitable for the simultaneous parallel testing of large numbers of samples in a rapid fashion. In addition, the relative automation of other areas of pathology testing makes the abovementioned prior art methods and apparatus even more disadvantageous by comparison.

SUMMARY OF THE INVENTION

It is an object of the present invention to provide an apparatus and method which will permit the simultaneous determination of completion times of chemical reactions, which produce an optical change, in large numbers of chemical samples.

According to one aspect of the present invention there is disclosed apparatus for simultaneously determining the completion time of chemical reactions, producing an optical change, in a plurality of chemical samples each of which is contained in a transparent container, said apparatus comprising retention means to locate the plurality of containers with each container interposed in a light path between a corresponding light source and a corresponding light sensor, an agitator insertable within said containers and movable to agitate said samples, and a timer connected with said light sensors and operable by the outputs thereof.

According to another aspect of the present invention there is disclosed a method of simultaneously determining the completion time, of a chemical reaction producing an optical change, in a plurality of chemical samples, said method comprising the steps of placing each said sample in a transparent container, initiating said reaction and simultaneously initiating timing means agitating said samples within said containers, and operating said timing means in response to an optical change in said samples. The operation of the timing means may be carried out manually or automatically.

BRIEF DESCRIPTION OF THE DRAWINGS

One embodiment of the apparatus of the present invention will now be described with reference to the drawings in which.

DETAILED DESCRIPTION

Figure 1:
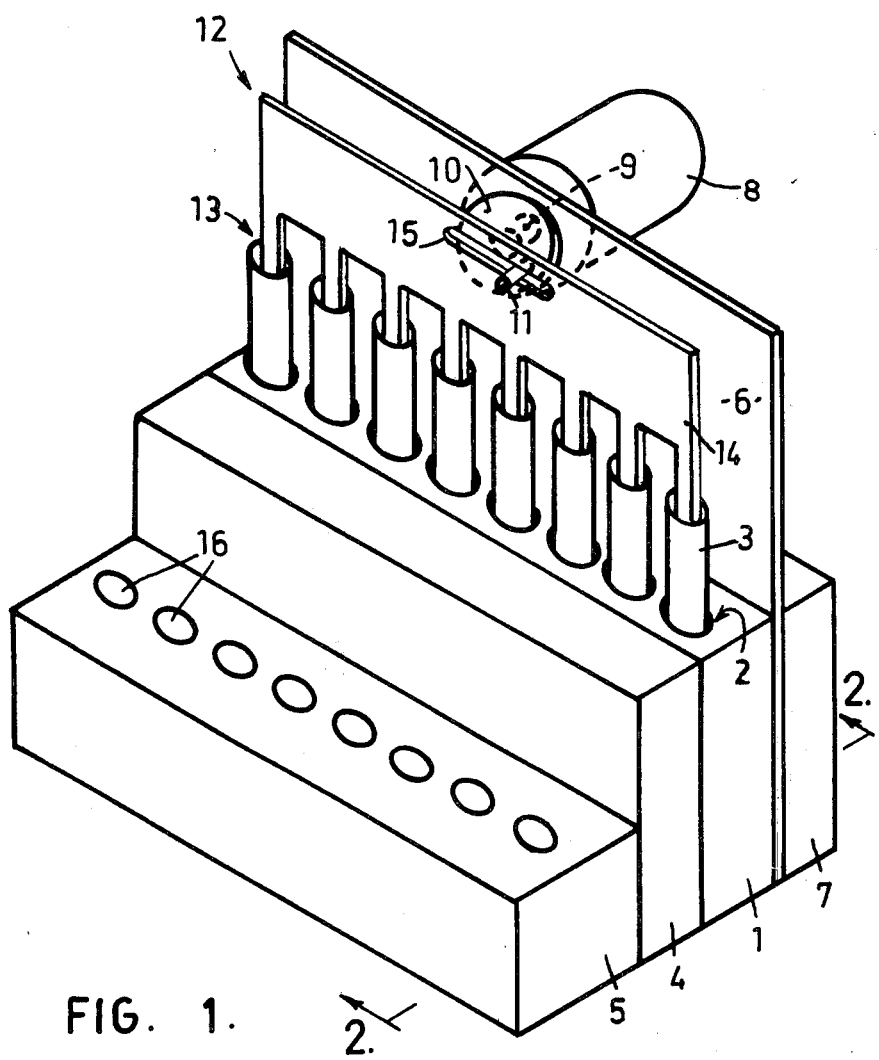
FIG. 1 is a perspective view of the apparatus of the preferred embodiment.

As seen in FIG. 1 the apparatus of the preferred embodiment comprises a metal block 1 having eight elongated recesses 2 each of which accommodates a test tube 3 made of glass or transparent plastic material. A sensor compartment 4 is located in front of the metal block 1 and a preheating body 5 is located in front of the sensor compartment 4.

To the rear of the metal block 1 is a vertically extending plate 6 to the rear of which is positioned a light source compartment 7. An electric motor 8 is mounted on the rearward side of the plate 6 and has a shaft 9 which extends through the plate 6. A disc 10 is centrally located on the shaft 9 and a pin 11 is mounted on the forward face of the disc 10 parallel to but spaced from the shaft 9.

An agitator comb 12, of flexible transparent plastic material having eight parallel spaced apart fingers 13 extending from a base 14, is located above the metal block 1 with each of the fingers 13 located inside a corresponding test tube 3. The base 14 has a transverse slot 15 extending therethrough within which the pin 11 is slidably located.

On rotation of the shaft 9, the pin 11 revolves thereby causing a vertical reciprocal oscillation of the comb 12. This vertical movement of the comb 12 agitates the contents of the test tubes 3 and the preferred rate of oscillation for the comb 12 lies within the range of from 5 to 20 cycles per second. Since the comb 12 is flexible it may be easily bent to disengage the pin 11 and slot 15 to permit removal of the comb 12. The comb 12 may then either be discarded or washed for re-use.

Figure 2:
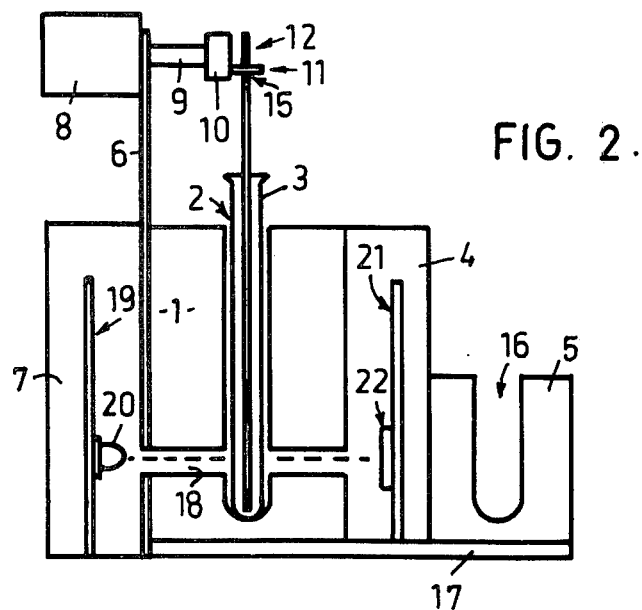
FIG. 2 is a cross-sectional view of the apparatus of FIG. 1 taken along the line 2-2 of FIG. 1.

The preheating body 5 contains eight recesses 16 similar to the recesses 2 and, as seen in FIG. 2, the preheating body 5, which is metal, is able to be heated by a heating plate 17 which heats both the preheating body 5 and metal block 1 to a predetermined temperature. The heating plate 17 preferably includes an electric element (not shown) and its associated temperature control circuitry (also not shown) is preferably located in compartment 7.

As also seen in FIG. 2, each recess 2 in the metal block 1 is transversely cut by a bore 18 which passes entirely through the metal block 1 and also through the plate 6 to provide a light path extending from the light source compartment 7 to the sensor compartment 4. A circuit board 19 is mounted within the light source compartment 7 and carries a light emitting diode (LED) 20 corresponding to each recess 2. A similar circuit board 21 is mounted within the sensor compartment 4 and carries eight light dependent resistors (LDR) 22. The LED'S 20 and LDR's 22 comprise a light source and light sensor respectively which enables a beam of light to be transmitted from the LED's 20 to the LDR's 22 when the contents of the test tube 3 are transparent.

Figure 3:
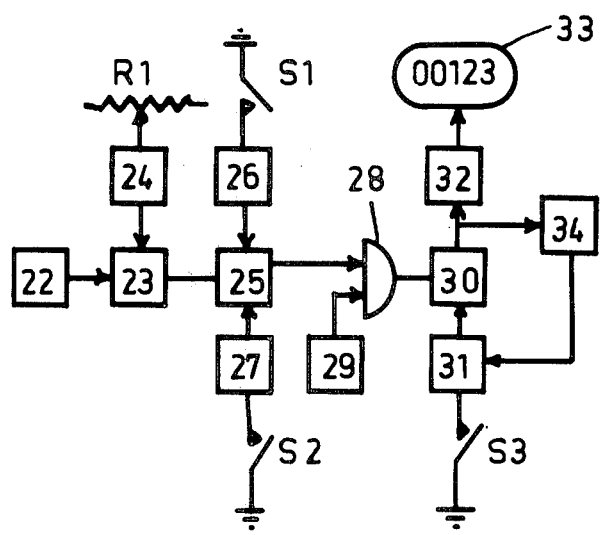
FIG. 3 is a schematic block diagram of the electronic timing circuitry associated with each light sensor of the apparatus of FIG. 1.

A schematic block diagram of the electronic timing circuitry associated with each light sensor 22 is illustrated in FIG. 3. The output from each light sensor 22 is directed to a corresponding comparator 23 which receives a reference signal from a voltage reference 24. The voltage reference 24 is adjustable by means of a variable resistor R1. The output of the comparator 23 is applied to a logic circuit 25 which controls the operation of a clock gate 28. A clock 29 has its output connected to the other input of the clock gate 28.

A manually operable switch S1 activates a control circuit 26 which provides a logic signal to the logic circuit 25 when it is desired to start the timer for the particular channel. Conversely, a manually operable switch S2 activates a similar control circuit 27 which provides a logic signal to the logic circuit 25 which results in the logic circuit 25 inhibiting the clock gate 28 to prevent the output of the clock 29 being passed to a counter 30 via the clock gate 28.

The output of the counter 30 is passed via a decoder 32 to a visual display 33 and is also simultaneously passed directly to a printer 34. A manually operable switch S3 activates a reset circuit 31 which provides a logic signal to the counter 30 to reset same. The printer 34 is also able to provide a signal to the reset circuit 31 when printing is completed and the counter 30 therefore is required to be reset.

The operation of the timing circuitry of FIG. 3 for a single channel is as follows. Firstly switch S3 is momentarily operated to reset the counter 30 and thereby reset the visual display 33 and prepare the printer 34 for printing a permanent record of the forthcoming test. When the reaction is initiated, the switch S1 is momentarily closed thereby causing control circuit 26 to instruct logic circuit 25 to permit clock gate 28 to pass the output of the clock 29 directly to the counter 30. In consequence the counter 30 begins counting and this is indicated both by the visual display 33 and the printer 34.

When the reaction is completed, the amount of light received by light sensor 22 is rapidly increased and this change is reflected in the output of the light sensor 22. In consequence the output of the light sensor 22 differs markedly from the reference signal provided by the voltage reference 24 and therefore the comparator 23 provides a signal to the logic circuit 25 to indicate that counting should cease. Accordingly, the logic circuit 25 disables the clock gate 28 thereby preventing the output from the clock 29 from reaching the counter 30. As a result, the counter 30 ceases to count and the count achieved during the time of the reaction is indicated both by the visual display 33 and the printer 34.

If for any reason it is necessary to manually stop the counter 30 this is done by momentarily operating switch S2 thereby causing control circuit 27 to instruct the logic circuit 25 to disable the clock gate 28 as before. It is to be understood that a similar circuit applies in relation to each of the light sensors 22 of the apparatus illustrated in FIGS. 1 and 2 save that a single clock 29 and a single printer 34 may be used for all the circuits associated with the plurality of light sensors 22. In addition, in such an arrangement, provision is made for operation of all the switches S1 simultaneously or individually as desired. Similarly the switches S2 and S3 may also be operated simultaneously or individually.

Some examples of the method of the present invention which are able to be carried out on the above described apparatus will now be described in more detail.

EXAMPLE 1

A method of conducting a coagulation screening test by determining the kaolin clotting time of haemolysate will now be described. The haemolysate, which is stable in a refrigerator for several hours, is first prepared by mixing 1 volume of citrated blood with 9 volumes of citrated plasma and then 6 volumes of water are added to each volume of the mixture. A volume of 0.7 ml of the above-desribed haemolysate mixture is then added to each of the test tubes 3 together with 0.1 ml of kaolin solution made up from 10 mg of kaolin per ml of approximately 0.9% or "physiological" saline solution.

The contents of the test tubes 3 are then activated by heating to 37° C as a result of placing the test tubes 3 in the recesses 2 of the metal block 1 for 6 to 8 minutes. During this time the contents of the test tubes 3 are agitated with continuous or intermittent action of the agitator comb 12. To recalcify the contents of the test tubes 3 and initiate the chemical reaction producing the optical change, a volume of 0.2 ml of M/40 calcium chloride ($CaCl_2$) solution is added to each test tube and the timing circuitry simultaneously activated. The contents of the test tubes 3 are continuously agitated by the agitator comb 12 and initially constitute a cloudy, substantially opaque suspension. The end point or completion time of the reaction is indicated by a sudden clearing of the suspension by the newly formed fibrin mesh, at which time the contents of the test tubes suddenly and rapidly become transparent. As the fibrin mesh forms it entraps the particles of the suspension and is swept away (formed into small relatively dense portions) by the agitator finger 13 thereby permitting the passage of light through the sample. Typically the end point of the reaction occurs approximately 45 seconds after the calcium chloride solution has been added.

The sudden increase in the passage light through the test tube when the contents become transparent, is sensed by the corresponding LDR 22 which operates the timing circuitry.

EXAMPLE 2

Determination of clotting time for kaolin-activated PTT. To each test tube is added 0.5 ml of buffered saline solution having a pH between 7 and 8, 0.1 ml of plasma, 0.1 ml of phospholipid and 0.1 ml of the kaolin solution referred to in Example 1 above.

The contents of the test tubes are activated at 37° C as before in Example 1 and again recalcified with 0.2 ml of M/40 calcium chloride solution. The clotting time following the recalcification of the contents of the test tubes is determined as before in Example 1.

EXAMPLE 3.

Determination of prothrombin time. To each test tube is added 0.6 ml of a suspension of a powder in buffered physiological saline solution having a pH between 7 and 8, the suspension having been formed from 1 mg of kaolin or 5–10 mg of Whatman CC 41 cellulose, per 1 ml of physiological saline. In addition 0.1 ml of plasma is added to each test tube. The contents of the test tube are then heated to 37° C as before.

To initiate the reaction 0.2 ml of premixed and preheated solution comprising thromboplastin and M/40 calcium chloride in equal proportions is added to each test tube. The clotting time is determined as described above in connection with Example 1.

Alternatively all reagents except the plasma are premixed and preheated and then the plasma is added last and the timing circuitry is simultaneously commenced.

The foregoing describes only some embodiments of the present invention and modifications, obvious to those skilled in the art, may be made thereto without departing from the scope of the present invention. For example, the LED's and LDR's could be replaced with incandescent bulbs and photo-electric cells respectively. Similarly the light source and light sensor may be located on the same side of the sample, in which case the light path would include a reflecting medium such as a mirror. In addition, reflected light from the cloudy suspension may be used to indicate the progress of the reaction rather than transmitted light. In this case the end point is indicated when the light sensor no longer receives a given quantity of reflected light.

As a further modification the timing and control circuitry described in FIG. 3, other than the light sensor 22, could be included in a microprocessor computer system. Also where a large number of samples are required to be tested in a given period of time, then automatic addition of reagents to the test tubes 3 via dispensing apparatus would be used. Such a dispensing apparatus would also include means in initiate the timing circuitry as the activating reagent was dispensed.

Although in the apparatus of the preferred embodiment, metal heating blocks have been disclosed, it is to be understood that fluid heating means such as a thermostatically controlled water bath may be used instead.

I claim:

1. Apparatus for simultaneously determining the completion time, of chemical reactions producing an optical change, in a plurality of chemical samples each of which is contained in a transparent container and includes a suspension containing fibrin and an added particulate substance to which fibrin is capable of adhering, said apparatus comprising retention means to locate the plurality of containers with each container interposed in a light path between a corresponding light source and a corresponding light sensor, and agitator insertable within said containers and movable to agitate said samples, a timer connected with said light sensors and operable by the outputs thereof, and means for switching on the timer, the latter means being operated with the commencement of the reaction in the containers, and means for stopping the timer constituted by the provision wherein, said particulate substance is so constituted that fibrin mesh formed by the samples during the chemical reaction traps the particles of said suspension and is swept away during agitation of the samples such that the timer is stopped by an increase of light to the detector.

2. 2. The apparatus as claimed in claim 1 wherein each said container has an open top, said retention means retains said containers upright and positioned in a row, and said agitator is transparent and comprises a comb having a base and a plurality of spaced parallel fingers, each of said fingers being insertable into a corresponding one of said containers via its open top.

3. The apparatus as claimed in claim 2 wherein the base of said comb has a slot therethrough transverse to said fingers and a pin is slidably positioned in said slot, said pin being substantially parallel to and displaced from a shaft, whereby rotation of said shaft produces longtudinal reciprocation of said fingers.

4. The apparatus as claimed in claim 3 including control means to maintain said samples at a constant temperature while said containers are located in said retention means.

5. The apparatus as claimed in claim 4 wherein said control means comprises a heated metal block, said retention means comprises an array of container receiving recesses in said block, said light sources are positioned to one side of said block, said light sensors are positioned on the other side of said block, and each said light path comprises a bore extending between said sides of said block and through the corresponding container receiving recess.

6. The apparatus as claimed in claim 5 including preheating means comprising a metal body in thermal communication with said heated block and including a like number of container receiving recesses.

7. A method of simultaneously determining the completion time, of a chemical reaction producing an optical change, in a plurality of chemical samples comprising a suspension containing fibrin, said method comprising the steps of adding to each sample a particulate substance to which fibrin is capable of adhering, placing each said sample in a transparent container, initiating said reaction and simultaneously switching-on a timing means, agitating said samples within said containers so that a fibrin mesh formed in the samples traps the particles of the suspension and the mesh is swept away during the agitation of the samples to cause the samples to be suddenly and rapidly rendered transparent, and switching-off said timing means when the samples are rendered transparent.

8. The method as claimed in claim 7 wherein each said container is placed in a corresponding light path between a corresponding light source and a corresponding light sensor, and said timing means is switched off in response to the outputs of said sensors.

9. The method as claimed in claim 8 wherein said samples are maintained at a pre-determined temperature while positioned in said light paths.

10. The method as claimed in claim 7 wherein said particles are kaolin, cellulose or diatomaceous earth.

11. The method as claimed in claim 10 wherein said containers have open tops and each said sample is agitated by longitudinal reciprocation of an elongated finger extending through the open top of the container holding said sample.

12. The apparatus as claimed in claim 3 wherein said pin is removable from said slot to enable separation of said comb from said shaft and removable of the comb from said containers.

* * * * *